United States Patent
Li et al.

(10) Patent No.: US 9,845,281 B2
(45) Date of Patent: Dec. 19, 2017

(54) METHOD FOR PREPARING HYDROXYETHYL (METH) ACRYLATE

(71) Applicant: Wanhua Chemical Group Co., Ltd., Yantai (CN)

(72) Inventors: Junping Li, Yantai (CN); Haibo Chen, Yantai (CN); Lichang Zhang, Yantai (CN); Chunxian Cui, Yantai (CN); Yuan Li, Yantai (CN); Weiqi Hua, Yantai (CN); Jiansheng Ding, Yantai (CN); Junhua Zhang, Yantai (CN); Zhaokun Cheng, Yantai (CN)

(73) Assignee: Wanhua Chemical Group Co., Ltd. (CN)

( * ) Notice: Subject to any disclaimer, the term of this patent is extended or adjusted under 35 U.S.C. 154(b) by 0 days.

(21) Appl. No.: 15/300,566

(22) PCT Filed: Jul. 29, 2014

(86) PCT No.: PCT/CN2014/083208
§ 371 (c)(1),
(2) Date: Sep. 29, 2016

(87) PCT Pub. No.: WO2016/008174
PCT Pub. Date: Jan. 21, 2016

(65) Prior Publication Data
US 2017/0183288 A1  Jun. 29, 2017

(30) Foreign Application Priority Data

Jul. 14, 2014  (CN) .......................... 2014 1 0334216

(51) Int. Cl.
*C07C 67/26* (2006.01)
*C08F 220/06* (2006.01)

(52) U.S. Cl.
CPC ............ *C07C 67/26* (2013.01); *C08F 220/06* (2013.01)

(58) Field of Classification Search
CPC ..................................................... C07C 67/26
See application file for complete search history.

(56) References Cited

FOREIGN PATENT DOCUMENTS

| CN | 101591245 | A | 12/2009 |
| CN | 101891613 | A | 11/2010 |
| CN | 102584579 | A | 7/2012 |
| CN | 101591245 | B | * 10/2012 |
| CN | 103304413 | A | 9/2013 |
| CN | 102584579 | B | * 12/2013 |

OTHER PUBLICATIONS

International Search Report for Application No. PCT/CN2014/083208 dated Apr. 22, 2015.

* cited by examiner

*Primary Examiner* — Paul A Zucker
(74) *Attorney, Agent, or Firm* — Lerner, David, Littenberg, Krumholz & Mentlik, LLP

(57) ABSTRACT

Hydroxyethyl (methyl)acrylate is prepared by a process of a combination of a three-stage tubular reactor and a tower reactor, wherein, firstly, a catalyst, a polymerization inhibitor and (methyl) acrylic acid are mixed until the solids are dissolved, then mixed with a part of ethylene oxide and thereafter enter into a first tubular reactor for a reaction, a reaction liquid flowing out from the first tubular reactor is mixed with a certain amount of ethylene oxide and enters into a second tubular reactor for a reaction, a reaction liquid flowing out from the second tubular reactor is then mixed with a certain amount of ethylene oxide and thereafter enters into a third tubular reactor, and a reaction liquid flowing out from the third tubular reactor is then passed through a stage of an adiabatic tower reactor and aged such that a product liquid is obtained from extraction.

24 Claims, 1 Drawing Sheet

METHOD FOR PREPARING HYDROXYETHYL (METH) ACRYLATE

CROSS REFERENCE TO RELATED APPLICATIONS

The present application is a national phase entry under 35 U.S.C. §371 of International Application No. PCT/CN2014/083208, filed Jul. 29, 2014, which claims priority from Chinese Patent Application No. 201410334216.1 filed Jul. 14, 2014, all of which are hereby incorporated herein by reference.

FIELD OF THE INVENTION

The present invention relates to the field of the preparation of hydroxyl acrylates, and specifically, the present invention relates to a method for preparing hydroxyethyl (meth)acrylate and the hydroxyethyl (meth)acrylate product prepared by the method.

BACKGROUND ART

Hydroxyethyl (meth)acrylate is a colorless and clear liquid with double functional groups in the molecules, and has a two-stage curing reaction function. It is one of the most valuable special (methyl)acrylates that has been studied mostly around the world. It is mainly used for the preparation of hydroxyl acrylic resins. The polymers of hydroxyethyl (meth)acrylate have special gloss, transparency and weather resistance. In the pharmaceutical industry, the autopolymers of hydroxyethyl methacrylate can be used for dental materials and orthopedics materials as they have no physiological rejections. With the development of the downstream industries, the application of the monomer is still increasing.

There are many methods for preparation of hydroxyethyl (meth)acrylate, and the common one used in the industrial production at present is the method of ring-opening reaction: in the reactor, EO is added dropwise to the (meth)acrylic acid as per a certain ratio of ethylene oxide (EO) and (meth)acrylic acid, and reacted to synthesize hydroxyethyl (meth)acrylate under the combined effect of a catalyst and a polymerization inhibitor.

CN101891613A discloses a method for preparing hydroxyethyl methacrylate: a flask equipped with a stirrer, a thermometer and a reflux condensing tube was placed on a water bath, ferric oxide, hydroquinone and methacrylic acid were added, the mixtures were heated to 80-85° C. by the water bath, the air in the flask was replaced by nitrogen, ethylene oxide was inlet after the ferric oxide was completely dissolved in the methacrylic acid, the time for inletting the ethylene oxide was 4 hours, the reaction was continued for 1 hour after the completion of the inletting of ethylene oxide, the reactants were then placed in a distillation flask, an appropriate amount of hydroquinone was added for reduced pressure distillation, and the fraction of 82-85° C. was collected as the product.

CN102584579A also discloses a preparation process of hydroxyethyl methacrylate characterized in that the reactor is vacuated by vacuum units and is kept in vacuum to make methacrylic acid, a catalyst, a polymerization inhibitor and water sucked to the reactor, then the vacuum degree of the reactor is kept between −0.99 Mpa and 0.75 Mpa, and then it is heated to 80-85° C., ethylene oxide is added dropwise, the pressure inside the reactor is ensured to be less than or equal to 60 KPa by controlling the dripping speed of the ethylene oxide, the dripping speed of the ethylene oxide need to be adjusted with continuing of the reaction and change of the reaction rate, and the reaction temperature is controlled at 90-100° C. by cooling with cooling water; after the completion of adding the ethylene oxide dropwise, the cooling water is shut off and the temperature is naturally raised, and sampling and detecting whether the mass percentage of methacrylic acid is less than 0.5 percent after the temperature is lowered, and if so, an addition reaction is deemed to be ended; and after the addition reaction is completed, the light component ethylene oxide, water and methacrylic acid are removed under reduced pressure, the intermediate product is transferred into a middle kettle, 0.5-5 wt % water is added, and then it is distilled under reduced pressure to obtain hydroxyethyl methacrylate.

The processes reported at present are mainly processes of batch tank type reactors. There are slight differences in the selection of process parameters such as a catalyst, a polymerization inhibitor, reaction temperature and reaction time. However, the reaction efficiency of the batch tank type reactors are low, and continuous production cannot be processed.

If the processes of stirring tank type reactors are used, the disadvantages are low reaction efficiency, a large amount of gas phase ethylene oxide and by-products such as diesters, monoesters, and static electricity is easy to be generated while the stirring rotating for a long time to easily cause the gas phase EO to explode, thus it is very dangerous; as the reaction progress, the reaction rate is changed, and the adding rate of EO needs to be adjusted at all times, so the operation is complex; and the cost of the investment of the devices are high. The problems of a very low reactant concentration and a very low reaction rate also exist for the continuous reactors, thus continuous production cannot be processed.

Although continuous production can be achieved by using tubular reactors, if stirring tank type reactors are simply replaced by the tubular reactors, when (meth)acrylic acid and EO are fed, the concentration of the EO is high, explosion will happens easily; the synthesis of hydroxyethyl (meth)acrylate is a strong exothermic reaction, and when the concentration of EO is high, the reaction rate will be too fast, thus too much heat will be released, there will be a risk of temperature runaway; and a too high concentration of EO will result in a further reaction between the generated hydroxyethyl (methyl)acrylate and EO to produce diglycol (meth)acrylate, causing the yield of the product to decrease; furthermore, under the condition of constant temperature, the conversion rate of (meth)acrylic acid and EO at the end of the reaction is low, a lot of (meth)acrylic acid is left, and it will be more difficult for the subsequent separation.

Therefore, a new process for preparing hydroxyethyl (meth)acrylate is needed to overcome the above disadvantages in the prior art.

DESCRIPTION OF THE INVENTION

One of the object of the present invention is to provide a new method for preparing hydroxyethyl (methyl)acrylate, to solve the problems in the present processes, and to provide hydroxyethyl (meth)acrylate product with improved product quality such as lower content of impurities. The present invention adopts a process of a combination of three tubular reactors and a tower reactor to independently control the operation condition (reaction temperature, pressure, residence time etc.) of each of the tubular reactors and the feeding amount of ethylene oxide as well as the operation condition of the tower reactor, and realizes the goals of decreasing the operation risk of the devices, achieving a continuous production, increasing the production efficiency and improving the quality of the product.

In order to achieve the above objects, the present invention adopts the following technical solutions:

A method for preparing hydroxyethyl (meth)acrylate by a process of a combination of a three-stage tubular reactors and a tower reactor, wherein, firstly, mixing catalysts, polymerization inhibitors and (meth)acrylic acid until the solids are dissolved, then being mixed with a part of ethylene oxide and thereafter entering a first tubular reactor to react; mixing the reaction liquid flowing out from the first tubular reactor i with a certain amount of ethylene oxide and entering thereafter a second tubular reactor to react; mixing the reaction liquid flowing out from the second tubular reactor with a certain amount of ethylene oxide and thereafter entering a third tubular reactor; aging the reaction liquid flowing out from the third tubular reactor in a tower reactor to obtain hydroxyethyl (meth)acrylate liquid product.

Specifically,

The solution of the present invention comprises mixing all of the catalysts, the polymerization inhibitors and (meth) acrylic acid until the solids are dissolved, then being mixed with ethylene oxide which represents 30-80%, preferably 50-70% of the total amount of ethylene oxide, and then adding them into a first tubular reactor to react; in the first tubular reactor, the reaction temperature is 80-120° C., preferably 90-110° C., the reaction pressure is 0.2-0.5 Mpa, preferably 0.3-0.4 Mpa and the residence time is 0.1-0.3 h, preferably 0.15-0.25 h. Because the EO concentration of this stage is high and the reaction rate is fast, the reaction rate can be efficiently controlled by adjusting the reaction temperature and the pressure to a relative low level, avoiding the produced product to further react quickly with EO and decreasing the content of by-products.

The reaction liquid that flows out from the first tubular reactor is mixed with ethylene oxide that represents 10-50%, preferably 20-40% of the total amount of ethylene oxide, and then enter the second tubular reactor to react; in the second tubular reactor, the reaction temperature is 100-130° C., preferably 110-120° C., the reaction pressure is 0.4-0.8 Mpa, preferably 0.5-0.7 Mpa and the residence time is 0.2-0.5 h, preferably 0.25-0.4 h; the EO concentration of this stage is low, and the dissolved quantity of EO in the liquid phase can be increased by increasing the pressure, thus increasing the probability of the reaction by the collision between EO and (meth)acrylic acid, ensuring the reaction to be carried out in a relative fast rate, and not resulting in increase of by-products and decrease of product yield.

The reaction liquid that flows out from the second tubular reactor is mixed with ethylene oxide that represents 1-30%, preferably 5-20% of the total amount of ethylene oxide, and then enter the third tubular reactor to react; in the third tubular reactor, the reaction temperature is 110-150° C., preferably 120-130° C., the reaction pressure is 0.5-1 Mpa, preferably 0.6-0.9 Mpa, and the residence time is 0.25-0.6 h, preferably 0.3-0.5 h; the concentrations of both (meth) acrylic acid and EO in this stage are low, the content of liquid phase EO is ensured by increasing pressure, and a more violent collision between the (meth)acrylic acid and the EO molecules can be achieving by increasing the reaction temperature, thus increasing the reaction rate and advantageously improving the conversion rate of (meth) acrylic acid and EO.

Finally, the reaction liquid that flows out from the third tubular reactor enters the tower reactor to be aged, and a liquid product is collected after the reaction. In the present invention, the tower reactor is preferably an adiabatic tower reactor, the theoretical plate number of the reactor is 4-20, preferably 6-15; the reaction pressure is 0.8-1.2 Mpa, preferably 0.9-1.1 Mpa; the residence time is 0.3-1 h, preferably 0.4-0.6 h; the content of the (meth)acrylic acid and the EO in the reaction liquid which flows out from the third tubular reactor is very low, and a high efficient mixing reaction cannot be achieved by a conventional reactor, however, because the contact areas of a tower reactor are large and the reaction liquid in the reactor is constantly collided and mixed, and the rest of gas phase EO which is in a small amount reacts with (meth)acrylic acid continuously in the tower reactor, the (meth)acrylic acid and the EO are nearly completely converted during a short residence time, the yield of the product is further increased, and the energy consumption for recovering monomers and the amount of three wastes are decreased.

In the method of the present invention, the tubular reactor is a constant temperature tubular reactor, and all of the tubular reactors are under the protection of $N_2$.

In the method of the present invention, for the whole reaction, the molar ratio of the total amount of ethylene oxide to (meth)acrylic acid is 1.0-1.2:1, preferably 1.03-1.1:1.

In the method of the present invention, the catalysts are one or more of amine compounds, iron compounds and chromium compounds; the amine compounds are selected from one or more of tetrabutyl ammonium bromide, tetramethyl ammonium bromide, tetramethyl ammonium chloride, tetrabutyl ammonium iodide, triethylamine and pyridine; the iron compounds are selected from one or more of ferric trichloride, iron powder, ferric formate, ferric acetate, iron acrylate and iron methacrylate; the chromium compounds are selected from one or more of chromium trichloride, chromium acrylate, chromium methacrylate, chromium acetylacetonate, chromium picolinate, chromium formate and chromium acetate; the amount of the catalysts is 0.1-2%, preferably 0.3-1% of the weight of (methl) acrylic acid.

In the method of the present invention, the polymerization inhibitors are selected from one or more of p-benzoquinone, p-phenylenediamine, phenothiazine, diisopropyl p-phenylene diamine, 4-hydroxy-2,2,6,6-tetramethyl-piperidinooxy and 4-carbonyl-2,2,6,6-tetramethyl-piperidinooxy; the amount of the polymerization inhibitors is 0.01-0.2%, preferably 0.05-0.15% of the weight of (methyl) acrylic acid.

In the method of the present invention, the mixing of the reaction materials in each stage of the reaction can be carried out in a jet mixer or a static mixer, preferably in a static mixer.

In the method of the present invention, a process of a combination of tubular reactors and a tower reactor is used. The reaction liquid after the three stage tubular reactors is further aged in the tower reactor, ensuring the conversion rate of (meth)acrylic acid to achieve the target level; the reaction liquid is obtained by a continuous extraction with a rate that is the same as that of the feeding; the process is a continuous process, and during the process, waste gases that are exhausted during the replacement of reactors for a batch process are not exhausted.

The advantages of the present invention lie in that: (1) a process of a combination of multi-stage tubular reactors and a tower reactor is used, the reaction time is shortened to about 1-2 h, and the reaction efficiency is increased dramatically; (2) the reaction conditions such as the temperatures, the pressures in the reactors are controlled separately, which ensure a fast reaction rate and a high conversion rate of the raw materials and reduce the occurrence of side reactions, the yield of the product is significantly improved, and the highest yield can be above 96%; (3) the leaking of ethylene oxide can be effectively avoided by a totally-enclosed condition for the addition reaction, reducing off-gas emissions and pollutions to the environment; the static electricity is effectively decreased and the safety and stability of the production is improved; (4) free radical inhibitors that do not need the corporation of oxygen are used, the efficiency of polymerization inhibition is high, and the contact between EO and oxygen can be effectively decreased; by the controlling solution of the present invention, the initial concentration of EO is low, under a low reaction temperature, the possibility of explosion by EO self-polymerization is decreased, thus the safety is improved; (5) a continuous production is achieved, the operation process is simplified, and the production efficiency is improved.

In the present invention, the "reaction pressure" is absolute pressure, hydroxyethyl (meth)acrylate is hydroxyethyl methacrylate or hydroxyethyl acrylate, and (meth)acrylic acid is acrylic acid or methacrylic acid.

DETAILED DESCRIPTION

The process provided by the present invention will be further illustrated by the following examples in which the preparation of hydroxyethyl methacrylate is described, however, the present invention is not limited thereby.

Figure 1:
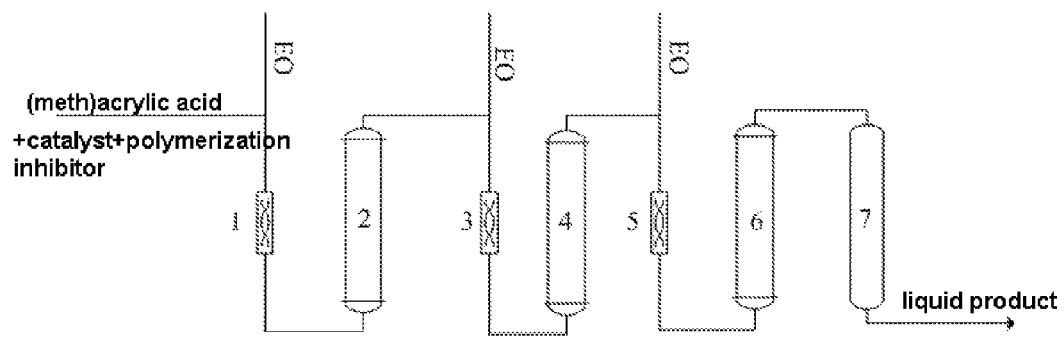
FIG. 1: a flow diagram of the method for preparing hydroxyethyl (meth)acrylate of the present invention; wherein, 1—the first static mixer; 2—the first tubular reactor; 3—the second static mixer; 4—the second tubular reactor; 5—the third static mixer; 6—the third tubular reactor; 7—a tower reactor.

According to the flow diagram shown in FIG. 1, the method for preparing hydroxyethyl methacrylate in the present invention adopts a combination of a three-stage tubular reactors and a tower reactor, wherein, firstly, catalysts, polymerization inhibitors and methacrylic acid are mixed until the solids are dissolved, then be mixed with a part of ethylene oxide in a first static mixer and thereafter are added into a first tubular reactor that is under the protection of $N_2$ to react, a reaction liquid flowing out from the first tubular reactor is mixed with a certain amount of ethylene oxide in a second static mixer and thereafter enter a second tubular reactor that is under the protection of $N_2$ to react, a reaction liquid flowing out from the second tubular reactor is then mixed with a certain amount of ethylene oxide in a third static mixer and thereafter enter a third tubular reactor that is under the protection of $N_2$, and a reaction liquid flowing out from the third tubular reactor is then passed through an adiabatic tower reactor and is aged such that a liquid product is extracted and obtained.

The analysis conditions for the gas chromatography in the present invention are as follows:

DB-5 nonpolar chromatographic column is used, ethanol as solvent is used, the temperature of a vaporizing chamber is 250° C., the flow rate of carrier gas is 1 ml/min, the sample size is 1 μL, and the temperature program of the chromatographic column: the temperature of 50° C. is maintained for 2 minutes, then it is increased to 80° C. at a rate of 5° C./min and it is maintained for 5 minutes, and then it is increased to 260° C. at a rate of 20° C./min and it is maintained for 15 minutes.

Unless specially indicated, the "%" in the following examples and comparative examples are all weight percent.

Example 1

A process of combining three tubular reactors with an adiabatic tower reactor was adopted, a 316L stainless steel pipe with a inner diameter of 0.02 m was used in the tubular reactors, the length of the first tubular reactor was 0.85 m, the length of the second tubular reactor was 1.40 m, the length of the third tubular reactor was 2 m, the tower reactor was a standard bubbling tower reactor, and the residence time of the materials in the adiabatic reactor was 0.5 h.

Figure 2:
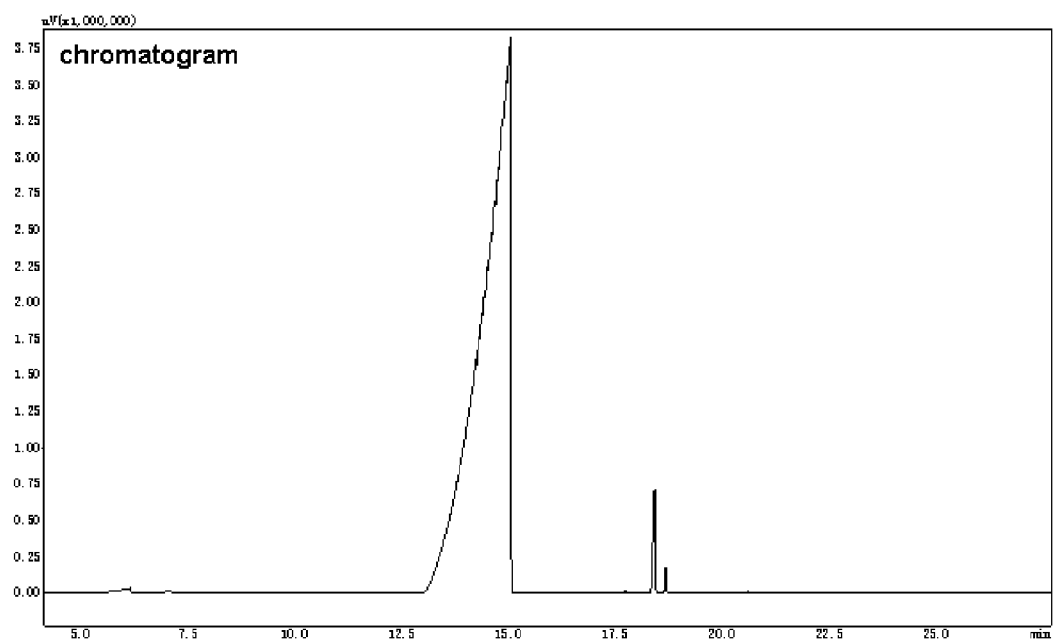
FIG. 2: a gas chromatography of the product liquid of example 1.

Firstly, 500 kg methacrylic acid, 2.5 kg chromium formate, 0.5 kg 4-hydroxy-2,2,6,6-tetramethyl-piperidinooxy (ZJ-701) were added into a mixing tank and were stirred until the solids were dissolved, and the solution of methacrylic acid raw material was obtained; EO was added respectively into three static mixers; the EO added into the first static mixer and the solution of methacrylic acid raw material were mixed in the first static mixer and then were conveyed to the first tubular reactor (it is called reactor 1 in the table below) that is under the protection of $N_2$, and the feeding rate of the solution of methacrylic acid raw material was 10 kg/h; the weight ratio of the EO respectively added into the first, the second and the third static mixer is 60:30:10, the molar ratio of the total amount of EO to MAA was 1.05, the feeding rate of the EO in the first tubular reactor was 3.22 kg/h, the feeding rate of the EO in the second tubular reactor (it is called reactor 2 in the table below) was 1.62 kg/h, and the feeding rate of the EO in the third tubular reactor (it is called reactor 3 in the table below) was 0.53 kg/h; the reaction temperature of the first tubular reactor was controlled at 100° C., the reaction temperature of the second tubular reactor was controlled at 115° C., and the reaction temperature of the third tubular reactor was controlled at 125° C.; the pressure of the first tubular reactor was 0.35 MPa, the pressure of the second tubular reactor was 0.60 MPa, and the pressure of the third tubular reactor was 0.80 MPa; the residence time of the first tubular reactor was 0.2 h, the residence time of the second tubular reactor was 0.35 h, and the residence time of the third tubular reactor was 0.4 h. The reaction liquid that had passed through the three tubular reactors entered the adiabatic tower reactor (it is called reactor 4 in the table below) and aged to convert the rest of methacrylic acid and ethylene oxide that were respectively in a small amount, the theoretical plate number of the tower reactor was 10, the reaction pressure was 1.0 MPa, the temperature of the outlet of the adiabatic reactor was 130° C., and the residence time was 0.5 h. After the completion of the reaction, the product was analyzed by gas chromatography for the composition of the product. The spectrum is shown in FIG. 2. The retention time of the samples: MAA 6.17 minutes, HEMA 14.86 minutes, DEGMMA (monoester by-product: diglycol methacrylate) 18.43 minutes, EGD-MAA (diester by-product: ethylene glycol dimethacrylate) 18.76 minutes. The analysis results are shown in table 1.

TABLE 1 the analysis result of the liquid product of example 1
The composition of the product

| MAA/% | HEMA/% | Monoester/% | Diester/% | Others/% |
|---|---|---|---|---|
| 0.36 | 96.52 | 2.47 | 0.21 | 0.44 |

Example 2

The difference between example 2 and example 1 lied in that the EO feeding ratios (i.e. the weight ratios of the EO respectively added into the first static mixer, the second static mixer, the third static mixer) was different, the effect of the ratios on the reaction performance was studied, and the other parameters were the same as that in example 1. The products were analyzed by gas chromatography. The results are shown in table 2.

TABLE 2 the analysis result of the liquid product of example 2

| EO feeding ratios | The composition of the products ||||| 
|---|---|---|---|---|---|
| | MAA/% | HEMA/% | Monoester/% | Diester/% | Others/% |
| 60:30:10 | 0.36 | 96.52 | 2.47 | 0.21 | 0.44 |
| 50:30:20 | 0.55 | 95.95 | 2.89 | 0.15 | 0.46 |
| 70:20:10 | 0.29 | 95.82 | 3.01 | 0.26 | 0.62 |
| 20:50;30 | 0.96 | 94.17 | 3.55 | 0.57 | 0.75 |

Example 3

The difference between example 3 and example 1 was that the present example provided the influence of different reaction temperatures on the reaction performance. The products were analyzed by gas chromatography. The results are shown in table 3.

TABLE 3 the analysis result of the liquid product of example 3

| The temperature of reactor 1/° C. | The temperature of reactor 2/° C. | The temperature of reactor 3/° C. | The composition of the products |||||
|---|---|---|---|---|---|---|---|
| | | | MAA/% | HEMA/% | Monoester/% | Diester/% | Others/% |
| 100 | 115 | 125 | 0.36 | 96.52 | 2.47 | 0.21 | 0.44 |
| 90 | 110 | 120 | 0.65 | 96.15 | 2.59 | 0.25 | 0.36 |
| 110 | 120 | 130 | 0.29 | 95.97 | 2.84 | 0.36 | 0.54 |
| 120 | 100 | 110 | 1.21 | 95.31 | 2.75 | 0.31 | 0.42 |

Example 4

The difference between example 4 and example 1 was that the present example provided the influence of different reaction pressures on the reaction performance. The products were analyzed by gas chromatography. The results are shown in table 3.

TABLE 4 the analysis result of the liquid product of example 4

| The pressure of reactor 1/MPa | The pressure of reactor 2/MPa | The pressure of reactor 3/MPa | The pressure of reactor 4/MPa | The composition of the products |||||
|---|---|---|---|---|---|---|---|---|
| | | | | MAA/% | HEMA/% | Monoester/% | Diester/% | Others/% |
| 0.35 | 0.60 | 0.80 | 1.0 | 0.36 | 96.52 | 2.47 | 0.21 | 0.44 |
| 0.40 | 0.70 | 0.90 | 1.1 | 0.34 | 96.1 | 2.89 | 0.31 | 0.36 |
| 0.3 | 0.5 | 0.6 | 0.9 | 0.65 | 95.92 | 2.65 | 0.22 | 0.56 |
| 0.6 | 0.3 | 1.0 | 0.7 | 1.51 | 94.75 | 2.85 | 0.36 | 0.53 |

Comparative Example 1

The process of a stirring tank type reactor:

500 kg methacrylic acid, 0.5 kg ZJ-701 and 2.5 kg chromium formate were added successively into the tank and were heated by steam until the temperature reached 85° C.; the air in the system was replaced by nitrogen; 268.6 kg ethylene oxide was added under the condition of 80-85° C. and the addition reaction was carried out for about 3 hours; the molar ratio of the ethylene oxide to the methacrylic acid was 1.05:1; after EO was added completely, it is aged for a 2 h to continuously react. A sample was taken out to test the weight percent of methacrylic acid, if the weight percent of the methacrylic acid was smaller than 0.5%, and then the addition reaction was deemed to be completed. After the completion of the reaction, the product was analyzed by gas chromatography. The results are shown in table 5.

TABLE 5 the analysis result of the liquid product of comparative example 1
The composition of the product

| MAA/% | HEMA/% | Monoester/% | Diester/% | Others/% |
|---|---|---|---|---|
| 0.48 | 94.04 | 4.20 | 0.70 | 0.58 |

The invention claimed is:

1. A method for preparing hydroxyethyl (meth)acrylate, conducted in a process using a combination of three-stage tubular reactors and a tower reactor, the process comprising the following steps:
   firstly, mixing catalysts, polymerization inhibitors and (meth)acrylic acid until the solids are dissolved;
   then mixing the mixture of the catalysts, polymerization inhibitors and (meth)acrylic acid with ethylene oxide in an amount of 30-80% of the total amount of the ethylene oxide in the whole reaction and thereafter entering a first tubular reactor to react;
   mixing the reaction liquid from the first tubular reactor with ethylene oxide in an amount of 10-50% of the total amount of the ethylene oxide in the whole reaction and thereafter entering a second tubular reactor to react;
   mixing the reaction liquid from the second tubular reactor with ethylene oxide in an amount of 1-30% of the total amount of the ethylene oxide in the whole reaction and thereafter entering a third tubular reactor; and
   aging the reaction liquid from the third tubular reactor in a tower reactor to obtain hydroxyethyl (meth)acrylate liquid product.

2. The method according to claim 1, wherein for the whole reaction, the molar ratio of the total amount of ethylene oxide to (meth)acrylic acid is 1.0-1.2:1.

3. The method according to claim 1, wherein the polymerization inhibitors are selected from one or more of p-benzoquinone, p-phenylenediamine, phenothiazine, diisopropyl p-phenylene diamine, 4-hydroxy-2,2,6,6-tetramethyl-piperidinooxy and 4-carbonyl-2,2,6,6-tetramethyl-piperidinooxy; the amount of the polymerization inhibitors is 0.01-0.2% of the weight of (meth)acrylic acid.

4. The method according to claim 1, wherein the catalysts are one or more of amine compounds, iron compounds and chromium compounds; the amine compound is selected from tetrabutyl ammonium bromide, tetramethyl ammonium bromide, tetramethyl ammonium chloride, tetrabutyl ammonium iodide, triethylamine and pyridine; the iron compound is selected from ferric trichloride, iron powder, ferric formate, ferric acetate, iron acrylate and iron methacrylate; the chromium compound is selected from chromium trichloride, chromium acrylate, chromium methacrylate, chromium acetylacetonate, chromium picolinate, chromium formate, chromium acetate; the amount of the catalysts is 0.1-2% of the weight of (meth)acrylic acid.

5. The method according to claim 1, wherein the amount of the ethylene oxide added into the first tubular reactor is 50-70% of the total amount of the ethylene oxide in the whole reaction; the amount of the ethylene oxide added into the second tubular reactor is 20-40% of the total amount of the ethylene oxide in the whole reaction; the amount of the ethylene oxide added into the third tubular reactor is 5-20% of the total amount of the ethylene oxide in the whole reaction.

6. The method according to claim 1, in the first tubular reactor, the reaction temperature is 80-120° C., the reaction pressure is 0.2-0.5 Mpa, and the residence time is 0.1-0.3 h.

7. The method according to claim 1, in the second tubular reactor, the reaction temperature is 100-130° C., the reaction pressure is 0.4-0.8 Mpa and the residence time is 0.2-0.5 h.

8. The method according to claim 1, in the third tubular reactor, the reaction temperature is 110-150° C., the reaction pressure is 0.5-1 Mpa, and the residence time is 0.25-0.6 h.

9. The method according to claim 1, during the reaction, each of the tubular reactors is under the protection of $N_2$.

10. The method according to claim 1, wherein the tower reactor is an adiabatic tower reactor.

11. The method according to claim 1, wherein the theoretical plate number of the tower reactor is 4-20; the reaction pressure is 0.8-1.2 Mpa; the residence time is 0.3-1 h.

12. The method according to claim 2, wherein the polymerization inhibitors are selected from one or more of p-benzoquinone, p-phenylenediamine, phenothiazine, diisopropyl p-phenylene diamine, p-hydroxy tetramethyl piperidine nitrogen oxygen free radical and p-carbonyl tetramethyl piperidine nitrogen oxygen free radical; the amount of the polymerization inhibitors is 0.01-0.2% of the weight of (meth)acrylic acid.

13. The method according to claim 2, wherein the catalysts are one or more of amine compounds, iron compounds and chromium compounds; the amine compound is selected from tetrabutyl ammonium bromide, tetramethyl ammonium bromide, tetramethyl ammonium chloride, tetrabutyl ammonium iodide, triethylamine and pyridine; the iron compound is selected from ferric trichloride, iron powder, ferric formate, ferric acetate, iron acrylate and iron methacrylate; the chromium compound is selected from chromium trichloride, chromium acrylate, chromium methacrylate, chromium acetylacetonate, chromium picolinate, chromium formate, chromium acetate; the amount of the catalysts is 0.1-2% of the weight of (meth)acrylic acid.

14. The method according to claim 2, wherein the amount of the ethylene oxide added into the first tubular reactor is 50-70% of the total amount of the ethylene oxide in the whole reaction; the amount of the ethylene oxide added into the second tubular reactor is 20-40% of the total amount of the ethylene oxide in the whole reaction; the amount of the ethylene oxide added into the third tubular reactor is 5-20% of the total amount of the ethylene oxide in the whole reaction.

15. The method according to claim 2, in the first tubular reactor, the reaction temperature is 80-120° C., the reaction pressure is 0.2-0.5 Mpa, and the residence time is 0.1-0.3 h.

16. The method according to claim 2, in the second tubular reactor, the reaction temperature is 100-130° C., the reaction pressure is 0.4-0.8 Mpa, and the residence time is 0.2-0.5 h.

17. The method according to claim 2, in the third tubular reactor, the reaction temperature is 110-150° C., the reaction pressure is 0.5-1 Mpa, and the residence time is 0.25-0.6 h.

18. The method according to claim 5, in the first tubular reactor, the reaction temperature is 80-120° C., the reaction pressure is 0.2-0.5 Mpa, and the residence time is 0.1-0.3 h.

19. The method according to claim 5, in the second tubular reactor, the reaction temperature is 100-130° C., the reaction pressure is 0.4-0.8 Mpa, and the residence time is 0.2-0.5 h.

20. The method according to claim 5, in the third tubular reactor, the reaction temperature is 110-150° C., the reaction pressure is 0.5-1 Mpa, and the residence time is 0.25-0.6 h.

21. The method according to claim 2, wherein for the whole reaction, the molar ratio of the total amount of ethylene oxide to (meth)acrylic acid is 1.03-1.1:1.

22. The method according to claim 6, in the first tubular reactor, the reaction temperature is 90-110° C., the reaction pressure is 0.3-0.4 Mpa and the residence time is 0.15-0.25 h.

23. The method according to claim 7, in the second tubular reactor, the reaction temperature is 110-120° C., the reaction pressure is 0.5-0.7 Mpa and the residence time is 0.25-0.4 h.

24. The method according to claim 8, in the third tubular reactor, the reaction temperature is 120-130° C., the reaction pressure is 0.6-0.9 Mpa and the residence time is 0.3-0.5 h.

* * * * *